United States Patent [19]

Kearney et al.

[11] Patent Number: 5,631,023
[45] Date of Patent: May 20, 1997

[54] METHOD FOR MAKING FREEZE DRIED DRUG DOSAGE FORMS

[75] Inventors: Patrick Kearney, Swindon; Sang K. Wong, New Malden, both of England

[73] Assignee: R.P. Scherer Corporation, Troy, Mich.

[21] Appl. No.: 481,287

[22] PCT Filed: Jul. 8, 1994

[86] PCT No.: PCT/US94/07618

§ 371 Date: Jun. 7, 1995

§ 102(e) Date: Jun. 7, 1995

[87] PCT Pub. No.: WO95/01782

PCT Pub. Date: Jan. 19, 1995

[51] Int. Cl.⁶ .................................................. A61K 9/20
[52] U.S. Cl. ..................... 424/465; 424/464; 424/473; 424/484
[58] Field of Search ........................... 424/465, 473, 424/22, 464, 484; 536/23

[56] References Cited

U.S. PATENT DOCUMENTS

| | | | |
|---|---|---|---|
| 4,305,502 | 12/1981 | Gregory et al. | 206/532 |
| 4,371,516 | 2/1983 | Gregory et al. | 424/22 |
| 4,749,790 | 6/1988 | Polomo-Coll et al. | 544/320 |
| 4,754,597 | 7/1988 | Buxton et al. | 53/440 |
| 4,758,589 | 7/1988 | Gregory | 514/774 |
| 4,894,459 | 1/1990 | Bod et al. | 548/197 |
| 4,946,684 | 8/1990 | Blank et al. | 424/441 |
| 5,021,582 | 6/1991 | Ballester-Rodes | 548/197 |
| 5,064,946 | 11/1991 | Shaver et al. | 536/23 |
| 5,075,114 | 12/1991 | Roche | 424/470 |
| 5,178,867 | 1/1993 | Guittard et al. | 424/473 |
| 5,206,072 | 4/1993 | Roche et al. | 424/464 |
| 5,215,756 | 6/1993 | Gole et al. | 424/484 |
| 5,275,823 | 1/1994 | France et al. | 429/489 |

FOREIGN PATENT DOCUMENTS

| | | |
|---|---|---|
| 903143667 | 7/1991 | European Pat. Off. . |
| 1548022 | 7/1979 | United Kingdom . |
| 2111423 | 7/1983 | United Kingdom . |
| 2114440 | 8/1983 | United Kingdom . |
| 2119246 | 5/1985 | United Kingdom . |
| 9311750 | 6/1993 | WIPO . |

*Primary Examiner*—Thurman K. Page
*Assistant Examiner*—William E. Benston, Jr.
*Attorney, Agent, or Firm*—McDonnell Boehnen Hulbert & Berghoff

[57] ABSTRACT

The present invention discloses an improved technique for preparing a rapidly dispersing pharmaceutic tablet of a granular therapeutic agent which has both relatively low solubility and relatively large particle size. Xanthan gum is added to a liquid admixture of solvent, carrier components, and the granular therapeutic agent. The xanthan gum not only facilitates suspension of the granular therapeutic agent in the liquid admixture, but, more surprisingly, does so without adversely effecting the dispersion qualities and texture of the tablet in the patient's mouth upon administration.

10 Claims, No Drawings

METHOD FOR MAKING FREEZE DRIED DRUG DOSAGE FORMS

This application is a 371 of PCT U.S. Ser. No. 94/07618.

BACKGROUND OF THE INVENTION

(1) Field of the Invention

This invention concerns an improved method for manufacturing a therapeutic tablet that dissolves nearly instantaneously upon contact with water. This method improves upon traditional freeze-dry methods which include preparing an aqueous suspension containing a granular therapeutic agent, placing the aqueous suspension in molds, and freeze drying the aqueous suspension to produce a solid pharmaceutic tablet. The improved method of this invention incorporates a particular agent into the aqueous gelatin containing suspension in order to keep the granular therapeutic agent uniformly dispersed, but does so without degrading the speed of dissolution or the texture and "feel" of the tablet upon dissolution in the mouth.

(2) Description of the Art

Many pharmaceutical dosage forms are administered orally in the form of solid, shaped articles such as tablets, pills, and capsules that retain their shape under moderate pressure. Generally these dosage forms are designed to be swallowed whole, chewed, or retained sublingually or bucally in order to deliver the medication. Some patients, particularly pediatric and geriatric patients, have difficulty swallowing or chewing solid dosage forms. To assist these patients, therapeutic compounds are sometimes provided as a liquid or suspension. However, these dosage forms are often difficult to distribute and store due to problems with stability. Other patients may not have water available at the time that they should take medication, and patient compliance is accordingly reduced. Still other patients resist taking medication, and may try to hide a solid pill in order to spit it out later.

The prior art discloses methods for manufacturing therapeutic tablets that immediately dissolve on contact with saliva in the mouth. Many of these prior art manufacturing methods involve freeze drying aqueous drug formulations. U.S. Pat. No. 4,371,516, discloses shaped articles, carrying pharmaceuticals, which disintegrate rapidly in the mouth. The shaped articles comprise an open matrix of carrier material, interspersed with the medicament. The articles may be prepared by subliming solvent from a composition comprising the medicament and the carrier material in solution, the solution being in a solid state in the mold.

This unique dosage form provides a solid tablet means for delivering medicaments which disintegrates on the tongue of a patient within 10 seconds or less. This rapid tablet disintegration rate makes the dosage form suitable for patients who have difficulty swallowing or refuse to swallow conventional tablets containing such medicaments. Further, the dosage form is exceptionally convenient since it does not require the aid of water in order to be swallowed. As such, the rapidly disintegrating nature of the dosage form and the convenience associated with its use offer dramatic improvement in patient compliance and treatment of disease states.

U.S. Pat. No. 4,305,502, discloses packages containing shaped articles carrying chemicals, particularly dosage forms carrying pharmaceuticals. The shaped articles, which disintegrate rapidly in saliva, are contained in depressions in sheets of filmic material and are enclosed by a covering sheet adhering to the filmic material. The shaped articles may be formed in the depressions by a sublimation process.

U.S. Pat. No. 4,758,598, discloses the preparation of solid shaped articles, particularly pharmaceutical dosage forms, by freezing a composition comprising a predetermined amount of chemical (e.g., a pharmaceutically active compound) and a carrier material solution in a mold, and then subliming solvent from the frozen composition. The side wall or walls of the mold are angled to minimize sublimation times.

U.S. Pat. No. 4,754,597 discloses the preparation of solid shaped articles, particularly rapidly dissolving pharmaceutical dosage forms. The articles carry predetermined unit quantities of chemicals and are made by a novel process involving the addition of the predetermined amount of chemical to a solid sublimed carrier article, prepared by freeze drying a carrier solution.

U.S. Pat. No. 5,188,825 discloses a freeze-dried dosage form that is prepared from a solution including a bulk forming agent and a therapeutic agent containing ion exchange resin having a particle size less than 90 microns. The bulk forming agent may be gelatin or xanthan gum. The bulk forming agent is added to the solution to maintain the dispersion of the active agent/ion exchange resin combination.

U.S. Pat. No. 5,206,025 discloses a porous pharmaceutical form and its method of preparation. The porous pharmaceutical form is prepared by freeze drying a solution including an active substance, binders, diluents, and additives. The binder includes xanthan gum, and gelatin in amounts to yield colloidal solutions.

U.S. Pat. No. 5,272,137 discloses an aqueous pharmaceutical suspension including microcrystalline cellulose and xanthan gum. The solution formed is capable of forming a suspension of particles ranging in size from 1 to about 850 microns.

Although these prior art freeze dried dosage forms offer many advantages over hard pills and capsules, the prior art dosage forms are limited in certain respects. For example, the prior art freeze dried dosage form were limited when used with medicaments that had both relatively low solubility in water and relatively large particle size. In such situations, the medicament tended to separate out of suspension too quickly during the manufacturing process, thereby forming an undesirable layer of sediment at the bottom of the tablet. Although the suspension could be extended by use of various thickening agents, these agents tended to degrade the dissolution characteristics of the tablet in the mouth.

SUMMARY OF THE INVENTION

This invention is directed to an improved technique for manufacturing a fast dissolving therapeutic tablet. It is an object of this invention to provide a method for preparing a fast dissolving therapeutic agent by freeze drying a liquid suspension containing a uniformly suspended granular therapeutic agent.

This invention is an improvement over prior art processes which provide the basic teaching for preparing freeze dried pharmaceuticals. As noted above, the basic teachings of this technology are set forth in U.S. Pat. Nos. 4,371,516; 4,305, 502; 4,758,598; and 4,754,597, the teachings of all of which are incorporated herein by reference. The manufacturing method uses a pre-prepared liquid composition including a solvent, a granular therapeutic agent, and a gelatin containing carrier material. The liquid composition is placed into one or more shaped depressions in a tray or mold to define liquid composition filled depressions. The liquid composition in the filled depressions is frozen, then the liquid portion of the liquid composition sublimed to define a solid medicament tablet. The solid medicament filled trays are then collected.

In the present invention, xanthan gum is added to the liquid composition, which is then stirred, prior to the freezing step. Xanthan gum behaves synergistically with gelatin as a flocculating agent to improve the ability of the liquid composition to suspend relatively large particles during the manufacturing process. More particularly, it is found that xanthan gum has the ability to improve the suspension qualities of the liquid composition without degrading the dissolution qualities and texture of the tablet in the mouth.

In a preferred embodiment, the invention comprises a method of producing a pharmaceutical tablet of famotidine, i.e., a medicament which functions as an $H_2$-antagonist. Treatment of the acid-related disorders of the upper gastrointestinal tract, such as reflux disease, often require life-long therapy with anti-secretary drugs, antacids, or $H_2$-antagonists such as famotidine. Conventional formulations of these medications are large, often difficult to swallow and may require water. These formulations are frequently inconvenient to use. This limitation may result in poor patient compliance and therefore ineffective therapy. Intravenous (IV) injection of medication is also commonly used, but this has the obvious disadvantages associated with direct transfer of a solution into the blood stream. In addition, professional medical care is generally required when drugs are introduced in this manner.

The delivery of famotidine or other $H_2$-antagonists using a rapidly disintegrating dosage form would be of tremendous advantage to the patients in need of such therapy. However, famotidine could not readily be formulated into the rapidly dispersing dosage form of the prior art because of the relatively low solubility and relatively large particle size of the medicament particles. These obstacles are overcome by the invention claimed herein.

DESCRIPTION OF THE CURRENT EMBODIMENT

The present invention relates to an improvement in a method of manufacturing a fast dispersing therapeutic tablet formulation. This therapeutic tablet is formed from a liquid admixture, or suspension, including an inert gelatin containing carrier material, a solvent, and a relatively insoluble therapeutic agent. The invention is particularly useful in relation to medicaments having a relatively low solubility and a relatively large insoluble particle size and density. The liquid admixture is filled into depressions in a tray, which are thereafter frozen solid. The solid admixture is then subjected to sublimation to produce a solid medicament tablet. The present method of manufacturing a solid medicament of this invention is an improvement over prior art processes in that a suspending agent is added to the liquid admixture in order to keep the relatively large and insoluble particles of granular therapeutic agent in suspension prior to freezing and sublimation.

Suspending agents, per se, are not new to pharmaceutical dosage forms in general. In the particular context of freeze dried medicaments, however, is has been found that suspending agents generally degrade the dissolution qualities of the tablet. For example, the suspending agent may result in a tablet which has a "gummy" texture in the mouth upon dissolution. The present invention overcomes that problem.

The method of this invention takes advantage of a synergism between xanthan gum and gelatin in which a small concentration of xanthan gum in the liquid admixture acts as a flocculating agent and cross-links the gelatin. The xanthan gum is a weak cross-linking agent that produces a transient cross linked gelatin containing solution that is stable when still and breaks up when disturbed. The gelatin, on the other hand, binds to and coats the granular therapeutic agent. The synergism between the xanthan gum and the gelatin creates a pourable suspension including a uniformly dispersed granular therapeutic agent. When the concentration of the xanthan gum falls below a minimum level, the xanthan gum insufficiently cross-links with the gelatin, and a portion of the granular therapeutic agent can fall out of suspension. When the xanthan gum concentration exceeds a certain maximum level then viscosity stabilization—keeping solids in solution by causing the solution to become viscous—predominates to keep the particles suspended with a commensurate degradation of the dissolution properties of the resulting freeze dried dosage form.

The general requirements for preparing a freeze dried tablet are well known in the art. The liquid admixture used to prepare the easily dissolvable medicament tablets of this invention comprises a solvent, a gelatin containing carrier material, a granular therapeutic agent, and a suspending agent. The carrier must be soluble in the chosen solvent. Additionally, the solvent must be inert to the therapeutic agent. However, the granular therapeutic agent need not be soluble in the solvent, although it may be soluble in the solvent to a limited degree.

Although the medicaments useful with this invention might be described as having relatively low solubility, the invention is by no means limited to medicaments which are considered to be technically "insoluble". Rather, the invention is most useful in connection with medicaments which, considering both mixing conditions and medicament concentration levels, remain at least partially in solid form, i.e., as a suspension of medicament in liquid, when the liquid admixture is filled into the tray depressions.

Water is preferably employed as the solvent in the liquid admixture, which is frozen and sublimed. An additional co-solvent, such as alcohol, may be used if it is desired to improve the solubility or the wetability of any of the ingredients in the composition. It is most preferred that the water is deionized water.

By "carrier material" is meant the dosage form excipients which provide the solid matrix support for the granular therapeutic agent after the solvent is sublimed. The medicament is incorporated within the matrix of the carrier material. The carrier material of this invention must include gelatin. Examples of suitable gelatin includes plain gelatin and gelatin that is partially hydrolyzed, for example by heating gelatin in water. For example, polysaccharide, plain gelatin, and hydrolyzed gelatin have each been tested in the system, and the improvements of adding xanthan gum have resulted in each. The preferred carrier material is hydrolyzed gelatin. Examples of other suitable carrier materials that can be combined with gelatin are those that are inert and pharmaceutically acceptable for use in preparing pharmaceutical dosage forms. Such carrier materials include polysaccharides such as dextran and polypeptides such as The liquid admixture also includes a granular therapeutic agent. The granular therapeutic agent may be any drug or therapeutic agent that has a therapeutic effect when administered to humans or animals. The term "granular therapeutic agent" includes agents having an average particle size ranging from as low as about 1 micrometers to about 400 micrometers. Any particulate therapeutic agent which remains at least partially in the solid state in the matrix of the carrier material may be used in the invention. For example, granular therapeutic agents that may be used in the liquid composition of this invention include various benzodiazepine compounds, acetaminophen and famotidine. In particular, this invention is useful in connection with formulations of famotidine, an $H_2$- antagonist having a particle size ranging from less than 1 micron to about 400 microns and more.

The granular therapeutic agents used in the liquid admixture have a tendency to settle to the bottom of both the vessels in which the liquid admixture is prepared and the depressions filled with the liquid composition. This settling effect results in a nonuniform medicament tablet. Therefore, the liquid admixture useful in this invention includes a suspending agent. The suspending agent cross-links the gelatin coated granular therapeutic agent and keeps the granular therapeutic agent dispersed in the liquid admixture until the time that the liquid admixture is frozen. Alternatively, when the chosen granular therapeutic agent is soluble in the solvents to a limited degree, the suspending agents aid in the solubilization of the therapeutic agent to produce a uniform liquid composition. "Suspending agents" includes any agent that facilitates preventing the settling of the granular therapeutic agent in the liquid admixture of this invention. A preferred suspending agent is xanthan gum, and is commercially available from, for example, Rhone-Poulenc, Cranbury, N.J. In preferred embodiments, xanthan gum comprises from about 0.001 to 1% by weight of the liquid admixture, and in particularly preferred embodiments, xanthan gum comprises from about 0.01 to about 0.05% by weight of the admixture. Above 0.05% by weight in a gelatin/famotidine carrier matrix, the xanthan gum acts predominantly as a viscosity modifier thereby retarding the dissolution properties of the resulting freeze dried dosage form.

The pH of the liquid admixture is also important and should be maintained at from a pH of from 4 to 8 to maintain the flocculating effect of the suspending agent. Preferably the pH of the liquid admixture is from 6 to 8 when the suspending agent is xanthan gum. Within this range, the charged therapeutic agent particles are surrounded by positively charged gelatin which in turn is cross-linked with a charged suspending agent such as xanthan gum. A suspending agent such as xanthan gum loses its flocculating effect outside of this narrow pH range.

As previously noted, this invention has particular advantages when used in conjunction with medicaments having a relatively large particle size and weight. That is, the invention is particularly useful in relation to medicaments whose particle size and weight cause them to settle out of suspension relatively quickly. The size and weight relationship may be, but is not necessarily, related to physical characteristics of the medicament in the dry condition. For example, as previously noted, medicaments may have a relatively large particle size and weight in the dry state, but may also have a low degree of solubility causing them to partially dissolve during preparation of the liquid admixture. Yet, depending on starting size and relative solubility, the particles may remain in solid particulate suspension to a significant degree and maintain a relatively large particle size and weight in suspension. Within this understanding, the present invention is directed to medicaments having a particular size and weight ratio in suspension. The average particle size of the medicament particle is generally greater than about 50 micrometers. In preferred form, the size of the medicament particles is between about 5 micrometers and about 400 micrometers.

Varying amounts of the $H_2$-antagonists or other antagonist may be included within the dosage form. For example, the dosage form may contain from about 1 mg to about 500 mg of famotidine. In preferred forms, the dosage form would contain either approximately 10, 20, 40 or 120 mg. of famotidine. The famotidine used in connection with the examples described herein had an average dry-state particle size of between about 20 micrometers and about 100 micrometers.

The liquid admixture useful in the method of this invention may contain other additional, optional ingredients. For example, the liquid admixture may include pharmaceutically acceptable adjuvants such as coloring agents, flavoring agents, preservatives, surfactants, and any other materials that can be incorporated into pharmaceutical preparations.

Among the coloring agents which may be employed are dyestuffs, pigments, and non-dispensable coloring agents. In the preferred embodiment, Opatint AD 25000, a micronized dispersion of red ferric oxide, available from Colorcon, Inc., West Point, Pa. The amount of coloring agent used in each dosage form may vary from about 0.08 mg to about 3.00 mg/dosage form.

Among the flavoring enhancers which may be employed are the following: banana, wild cherry, peppermint, strawberry, aniseed, black currant, grapefruit, caramel, raspberry, lemon, tutti frutti, cinnamon, lime, orange, spearmint, eugenol or any combination of these flavoring ingredients. In the preferred embodiment, aspartame, obtained from Forum Chemicals, Ltd., Forum House, 41 Brighton Road, Redhill, Surrey, U.K., and peppermint oil or powder, obtained from Firmenich U.K., Ltd., Hays Road, Southhall, Middlesex, U.K., were combined in a ration of about 15:1 to introduce an acceptable flavor to the final solid dosage form. The total amount of flavor enhancer may range from about 0.10 mg to about 2.50 mg/dosage form.

The liquid admixture of this invention is typically prepared in a large batch and the batch is divided into small controlled doses by filling the liquid admixture into one or more shaped depressions in a molded tray. Generally, the shape of the depression will correspond to the size and shape of the desired dosage form. A plurality of shaped depressions will generally be formed in a sheet of filmic material. For example, the filmic material may be made of a thermoplastic material with the depressions formed by thermal forming.

The type of filmic material used is not critical to the instant invention. However, the filmic material should resist the transmission of to moisture and the filmic material should be compatible with a cover or with some other means for sealing the depression containing filmic material from the environment. The filmic material is generally the same or similar to the material use in conventional blister packs. Among the filmic materials that may be utilized are the following: polyvinyl chloride, laminates of filmic material such as polyvinyl chloride/polyvinylidene chloride, polyvinyl chloride/polytetra-fluoroethylene or polyvinyl chloride/polyethylene/polyvinylidine chloride. The filmic material may also be prepared from polypropylene which may be used alone or in conjunction with polyethylene terephthalate glycol and other non-chlorinated materials. Other materials which have suitable integrity, are inert towards the formulation and have the thermal stability required to withstand the freeze cycle and sublimation process are also included within the scope of this invention.

The liquid admixture may be filled into the depressions by any means known to the art. Similarly, the liquid filled depressions may be frozen by any method known in the art capable of producing a sublimable frozen article. Preferably, the liquid admixture is frozen in a liquid nitrogen or a liquid carbon dioxide freezer. The freezer should operated at a temperature that is low enough to completely solidify the admixture.

The frozen solvent portion of the admixture is preferably thereafter sublimed. Sublimation is preferably achieved in a freeze-drier by subjecting the now-solid admixture in the depression to a reduced pressure, followed by controlled application of heat to aid the sublimation. At this point the freeze drier temperature may be adjusted upward to speed up sublimation. When the sublimation is complete, the freeze drier is pressurized to atmospheric pressure and the now solid medicament tablets are removed from the freeze drier and recovered. The solid medicament tablets may be recovered by removing them from the depressions or by sealing the solid medicament tablets into the depression with, for example, a sheet of plastic film that is thermally or adhesively attached to the depression filled tray.

EXAMPLES

A fast dissolving, solid, oral, medicament tablet, delivering about 10, 20 or 40 mg of famotidine per dosage form, was prepared using the following procedures.

Example 1

Preparation of Premix

The ingredients of Table 1 were added to a mixing bowl and dry mixed for five (5) minutes:

TABLE 1

| | CARRIER MATERIAL | | |
| --- | --- | --- | --- |
| | Amount Used for Stated Potency | | |
| Ingredient | 10 mg | 20 mg | 40 mg |
| Gelatin | 577.98 g | 540.00 g | 540.00 g |
| Mannitol | 765.00 g | 490.90 g | 490.86 g |
| Xanthan Gum | 5.94 | 5.40 g | 5.40 g |

Water was added to the mixing bowl and the ingredients were mixed until a uniform paste was obtained. The amount of water used to prepare the suspension is shown in Table 2.

TABLE 2

| | WATER REQUIREMENT | | |
| --- | --- | --- | --- |
| | Amount H$_2$O Used for Stated Potency | | |
| Stated Potency | 10 mg | 20 mg | 40 mg |
| Paste Production | 1.60 kg | 1.60 kg | 1.60 kg |
| Dilution Step | 13.818 kg | 13.510 kg | 13.377 kg |

A partial vacuum of about 0.8 to about 0.9 bar was applied to the mixing bowl and the amount of deionized water for the dilution step, shown in Table 2, was added. The mixture was stirred under vacuum for an additional 15 minutes.

The mixture was then heated to 40±2° C. and homogenized for 10 minutes while maintaining the partial vacuum of about 0.8 to about 0.9 bar. The homogenized mixture was cooled to about 23±1° C. and filtered through a 38 micron filter.

In a separate mixing bowl, the amount of Opatint AD 25000 shown in Table 3, and the amount of deionized water shown in Table 3, were mixed and sonicated until the Opatint suspension was fully dispersed. This suspension was then added to the mixture containing gelatin, mannitol and xanthan gum prepared previously.

TABLE 3

| COLORING AGENT PREPARATION | | |
| --- | --- | --- |
| Potency | Opatint AD 25000 | Water |
| 10 mg/lozenge | 54.00 g | 240 g |
| 20 mg/lozenge | 7.20 g | 200 g |
| 40 mg/lozenge | 90.00 g | 250 g |

The mixture containing the Opatint was then homogenized under a partial vacuum of about 0.8 to about 0.9 for about 5 minutes.

Example 2

Preparation of Famotidine Suspension

In processing the 10 mg dosage form, about 3 kg of the premix were transferred to a mixing vessel containing a homogenizer. While homogenizing the premix, 782.64 g of famotidine were gradually added to this portion of the premix. Once the famotidine was completely dispersed, the suspension was transferred to a mixer and mixed under a partial vacuum of about 0.8 to about 0.9 bar to assure adequate deaeration of the suspension. The formulation was brought to ambient pressure and an amount of aspartame and peppermint flavor as shown in Table 3, were added to the suspension of the remainder of the premix was added with stirring. The final mixture was homogenized under a partial vacuum of about 0.8 to about 0.9 bar for 10 minutes. The resulting suspension was transferred to a storage vessel.

In processing the 20 and 40 mg dosage forms, the procedure was modified to assure uniform mixing of the increased amount of famotidine in the final formulation. For these potencies, about 3 kg of the premix were transferred to a mixing vessel containing a homogenizer. While homogenizing the premix, about 700 g of famotidine were gradually added to this portion of the premix. This step was repeated using a further 3 kg quantity of premix and an additional 740 g of famotidine. Once the drug was fully dispersed, the total suspension was transferred to a vessel and homogenized together for 10 minutes. The suspension was then transferred to a mixer under a partial vacuum of about 0.8 to 0.9 bar to assure adequate deaeration of the suspension. The formulation was brought to ambient pressure and the amount of aspartame and peppermint flavor shown in Table 3 were added to the suspension and the remainder of the premix was added with stirring. The final mixture was homogenized under a partial vacuum of about 0.8 to about 0.9 bar for 10 minutes. The resulting suspension was transferred to a storage vessel.

TABLE 4

| ASPARTAME AND PEPPERMINT FLAVOR REQUIREMENTS | | |
| --- | --- | --- |
| Potency | Aspartame | Peppermint Flavor |
| 10 mg/lozenge | 146.70 g | 9.72 g* |
| 20 mg/lozenge | 135.00 g | 72.00 g** |
| 40 mg/lozenge | 135.00 g | 72.00 g** |

*The peppermint flavor used for the 10 mg lozenge was provided as an oil.
**The peppermint flavor used for the 20 and 40 mg lozenges was provided as a powder.

Example 3

Filling and Freeze Drying of the Suspension

An amount of suspension (shown in Table 4) was dispensed into each depression in a polyvinyl chloride tray. The depressions were cylindrical in nature having volumes and diameters shown below. There were 100 to 180 depressions in each tray. The tray was then moved through a freeze tunnel which was maintained at a temperature of from about −20° C. to about −160° C. to assure that the dosage forms were completely frozen.

TABLE 4

WEIGHT OF SUSPENSION DISPENSED PER LOZENGE.

| Potency | Weight Dispensed | Depression Volume | Depression Dia. |
|---|---|---|---|
| 10 mg/lozenge | 0.23 g | 230 mL | 12 mm |
| 20 mg/lozenge | 0.25 g | 250 mL | 12 mm |
| 40 mg/lozenge | 0.50 g | 500 mL | 16 mm |

As the trays emerged from the freeze tunnel, they were either stored at about −20° C. or placed immediately into the freeze drier.

The shelf of the freeze drier is maintained at a temperature of from about −20° C. to about −10° C. Once the sublimation process was initiated, a partial vacuum of about 0.25 to about 1.00 m bar was applied within the freeze drier.

Example 4

Disintegration Testing

Samples of the dosage forms prepared using the procedures stated in the Examples above were tested for disintegration time as follows: Five breakers filled with distilled water are placed in a water bath controlled at 37° C. Five dosage forms are each secured in a wire clip weighing 0.5 g plus or minus 0.05g. The weighted dosage forms are each placed in a discrete tube in a gauze covered basket. The baskets are then lowered at a constant rate into the breakers, one basked to a breaker. The disintegration time is measured from starting the raising and lowering mechanism to the time the last dosage form disintegrates. Disintegration is complete when the wetted mass has passed through the gauze, or the gauze is visible through the remaining mass. As the data in Table 1 indicate, each of the dosage forms tested disintegrated within 10 seconds.

FAMOTIDILNE ZYDIS DISINTEGRATION TIMES

| | Disintegration Time (Seconds) |
|---|---|
| | 20 mg 12 mm Formula |
| Batch 1 | 1.09 |
| Batch 2 | 1.85 |
| Batch 3 | 1.68 |
| *Mean | 1.54 |
| | 40 mg 16 mm Formula |
| Batch 1 | 1.09 |
| Batch 2 | 1.18 |
| Batch 3 | 1.30 |
| *Mean | 1.19 |

*The two decimal figures should not be taken as indicative of the accuracy of the timing. This is simply the value recorded by the stop-watch which is controlled by hand.

Example 5

Rate of Solution Samples of the dosage form prepared using the procedure outlined above were tested for rate of solution using the USP Apparatus 2 (paddles) (U.S. Pharmacopeia, XXII p.1578.) The testing was conducted using 900 ml of distilled, deionized water which was maintained at 37°±0.5° C. throughout the testing period. Famotidine was determined by reverse phase HPLC using a Hypersil column with a mobile phase of 7% $CH_3CN$ in $CH_3COONa$ (pH 8.0) with a UV detection at 270 nm. Results from each of four formulations of famotidine are presented in Table 5. These results demonstrate both the uniformity of the $H_2$-antagonist and also the rapid delivery capability of the dosage form.

TABLE 5

RATE OF SOLUTION OF FAMOTIDINE FREEZE DRIED LOZENGE
Average % of Claim Famotidine dissolved at Stated Time

| Potency | 2 min. | 5 min. | 8 min. |
|---|---|---|---|
| 10 mg/lozenge | 79% | 87% | 101% |
| 20 mg/lozenge | 83% | 95% | 100% |
| 40 mg/lozenge | 83% | 95% | 99% |

Example 6

Uniformity of the Dosage Form

In order to demonstrate the uniformity of the resulting dosage form, ten lozenges from each of four different potencies of freeze dried lozenges containing famotidine were tested by dissolving the dosage forms in 0.01M pH 7 phosphate buffer and quantifying the dissolved famotidine using HPLC with a Hypersel $C_{18}$, 15 cm column maintained at 40° C. with a mobile phase of acetonitrile and 0.1M sodium acetate buffer at pH 6.0. UV detection was utilized at a wavelength of 275 nm. The results of this study are shown in Table 6.

TABLE 6

DOSAGE FORM UNIFORMITY
mg/Lozenge

| Potency | Range | Average |
|---|---|---|
| 10 | 9.7–10.4 | 10.1 |
| 20 | 20.0–21.0 | 20.5 |
| 40. | 40.7–41.8 | 41.1 |

These results clearly show that xanthan gum produces solid medicament tablets of uniform dosage.

The foregoing specification provides a description of certain aspects of the invention in relation to particular preferred embodiments. It is contemplated, however, that the invention may find use and be adopted for use in applications and embodiments other than those described herein. Accordingly, the invention is to be limited only by the following claims and their equivalents.

What is claimed is:

1. A method of manufacturing a solid, shaped dosage form which disintegrates in lass than about 10 seconds upon contact with an aqueous media, said method including the preparation of a liquid admixture comprising a solvent, gelatin, a granular therapeutic agent having a particle size ranging from about 1 to about 400 microns and from 0.01 to 0.05 weight percent xanthan gum sufficient to act predominantly as a gelatin flocculating agent; filing said liquid admixture into one or more shaped depressions in a tray; freezing said liquid admixture in said trays so as to form solid shaped admixtures of solvent, carrier and granular therapeutic agent; and removal of said solvent so as to form a solid shaped tablet of carrier matrix and granular therapeutic agent.

2. The method of claim 1 wherein xanthan gum is added to the liquid admixture prior to the addition of the granular therapeutic agent to said liquid admixture.

3. The method of claim 1 wherein the solvent used to prepare the liquid admixture comprises an aqueous solvent.

4. The method of claim 1 wherein the solvent used to prepare the liquid admixture is removed by freeze drying.

5. The method of claim 1 wherein the granular therapeutic agent is famotidine.

6. The method of claim 1 wherein the pH of the admixture is from 6.0 to 8.0.

7. A method for manufacturing a solid, shaped pharmaceutical dosage form which disintegrates in less than about 10 seconds upon contact with an aqueous media by the steps comprising preparing a liquid admixture including a solvent, gelatin, famotidine having a particle size range of from about 0 to about 400 microns, and xanthan gum in an amount from about 0.01 to 0.05 weight percent of the carrier matrix; filling said liquid admixture into one or more shaped depressions in a tray; freezing said liquid admixture in said tray so as to form a solid shaped admixture of solvent, carrier and granular therapeutic agent; and removal of said solvent so as to form a shaped tablet of carrier matrix and granular therapeutic agent.

8. The improved pharmaceutical dosage form of claim 7 wherein xanthan gum is added to the liquid admixture prior to the addition of the granular therapeutic agent to said liquid admixture.

9. The improved pharmaceutical dosage form of claim 7 wherein the pH of the admixture is from about 6 to about 8.

10. A solid, shaped famotidine dosage form made by preparing a liquid admixture having a pH of from 6 to 8 comprising a solvent, gelatin, famotidine having a particle size of from i to 400 microns, and xanthan gum in an amount ranging from about 0.01 and 0.05 percent by weight of the carrier matrix; filling said liquid admixture into one or more shaped depressions in a tray; freezing said liquid admixture in said tray so as to form a solid shaped admixture of solvent, carrier and famotidine; and removal of said solvent so as to form a shaped tablet of carrier matrix and famotidine.

* * * * *